US 7,235,270 B2

(12) United States Patent
Mayeux

(10) Patent No.: US 7,235,270 B2
(45) Date of Patent: Jun. 26, 2007

(54) PAIN BALM

(76) Inventor: Jerry V. Mayeux, HC 66 Box 74, Deming, NM (US) 88030

( * ) Notice: Subject to any disclaimer, the term of this patent is extended or adjusted under 35 U.S.C. 154(b) by 0 days.

(21) Appl. No.: 10/797,983

(22) Filed: Mar. 10, 2004

(65) Prior Publication Data

US 2004/0185126 A1  Sep. 23, 2004

Related U.S. Application Data

(60) Provisional application No. 60/453,548, filed on Mar. 10, 2003.

(51) Int. Cl.
*A61K 36/00* (2006.01)
(52) U.S. Cl. ................................. 424/760
(58) Field of Classification Search ............ 424/760
See application file for complete search history.

(56) References Cited

U.S. PATENT DOCUMENTS

| 4,486,450 A |   | 12/1984 | Bernstein |
| 4,536,404 A |   | 8/1985  | Bernstein |
| 5,972,642 A | * | 10/1999 | Flen.o slashed. et al. ..... 435/67 |
| 6,074,687 A | * | 6/2000  | Todd .......................... 426/638 |
| 6,197,823 B1 |  | 3/2001  | Barr et al. |

| 2001/0002406 A1 | 5/2001 | Robbins |
| 2001/0011083 A1 | 8/2001 | Barr et al. |

FOREIGN PATENT DOCUMENTS

| GB | 2191929 A | * | 12/1987 |
| JP | 08099813 A | * | 4/1996 |

OTHER PUBLICATIONS

Chattem, "Capzasin-HP", *Product packaging for arthritis pain relief*, Capzasin-HP contains purified capsaicin, natural ingredient; Capsaicin (0.075%),(2000).
Dewitt, Dave, "The Chile Pepper Encyclopedia", William Morrow and Company, New York, (1999), 118-136.
Dewitt, Dave, et al., "The Healing Powers of Peppers", Three Rivers Press, New York, NY, 1982, pp. 92-131, with Chile Pepper recipes and fork remeedies for bette health and living,(1998),92-131.
Dewitt, Dave , et al., "The Whole Chile Pepper Book", Little, Brown and Company, Boston, (1990),76-79; 182-183.
Stiefel, "Capsagesic-HP", *Product packaging for Capsagesic-HP Cream*, Capsagesic-HP Cream contains capsicum oleoresin (Capsaicin 0/075%),(2000).

* cited by examiner

*Primary Examiner*—Christopher Tate
*Assistant Examiner*—S. B. McCormick-Ewoldt
(74) *Attorney, Agent, or Firm*—Vidal A. Oaxaca; Deborah A. Peacock; Peacock Myers, P.C.

(57) ABSTRACT

The present invention comprises a pain balm comprising a fermentation extract of the cultivar of the genus *capsicum*.

20 Claims, No Drawings

PAIN BALM

This application claims the benefit of the filing of U.S. Provisional Patent Application Ser. No. 60/453,548, entitled "Pain Balm", filed on Mar. 10, 2003, and the specification thereof is incorporated herein by reference.

BACKGROUND OF THE INVENTION

1. Field of the Invention (Technical Field)

The present invention comprises a pain balm comprising a fermentation extract of a cultivar of the genus *capsicum*.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Methods and compositions for providing topical pain relief are known. Typically, these involve the use of ground capsaicin in a medium. However, none appear to subject capsaicin to the effects of microbial fermentation.

BRIEF SUMMARY OF THE INVENTION

The present invention is directed to a topical pain relief composition and method of making the topical pain relief composition.

The composition of the present invention preferably comprises a capsaicin fermentation extract and an oil. The capsaicin in the extract is preferably derived from *Capsicum chinense* although other capsaicin species may be utilized in the present invention.

The fermentation extract preferably comprises capsaicin and volatile, oil soluble fermentation products and by-products. The oil preferably comprises vegetable oil, butter, margarine, lard, petrolatum, mineral oil, paraffin, wax, liquid hydrocarbon, semi-solid hydrocarbon, and/or a combination thereof, although the invention is not limited to these oils. If a vegetable oil is used, the preferred vegetable oil comprises corn oil, canola oil, peanut oil, soy oil, palm oil, sesame oil, and/or a combination thereof, although the invention is not limited to these vegetable oils. The oil is preferably in a ratio of between approximately 5 and approximately 10,000 parts of the oil to one part of the capsaicin fermentation extract.

The invention is further directed to a yeast culture inoculum for use in a capsaicin fermentation medium for the preparation of a topical pain treatment. This yeast culture inoculum initially comprises a *Capsicum* sp. cultivar in water, a yeast, and a nutrient mixture.

The nutrient mixture preferably comprises nitrogen, phosphorus, potassium, and/or a combination thereof, and most preferably 20-20-20 nitrogen-phosphorus-potassium. The nutrient mixture preferably comprises an amount of between approximately 5% and approximately to 10% by volume; and most preferably comprises an amount of between approximately 1% and approximately 2% by volume.

The *Capsicum* sp. cultivar preferably comprises 1 part *Capsicum* sp. cultivar to an amount of between approximately 1 and approximately 120 parts water; more preferably 1 part *Capsicum* sp. cultivar to an amount of between approximately 10 and approximately 40 parts water; and most preferably 1 part *Capsicum* sp. cultivar to an amount of between approximately 15 and approximately 30 parts water.

The yeast in the inoculum preferably comprises an amount of between approximately 0.1% and approximately 50% by volume; more preferably an amount of between approximately 0.1% and approximately 50% by volume; and most preferably an amount of between approximately 1% and approximately 20% by volume.

The present invention is also directed to a capsaicin fermentation medium for the preparation of a topical pain treatment. This medium preferably comprises a *Capsicum* sp. cultivar in water, a carbohydrate, a yeast culture inoculum, and a nutrient mixture (such as described above).

The fermentation medium may further comprise a second nutrient mixture, comprising calcium, magnesium, iron, zinc and/or a combination thereof, although the invention is not limited to these particular nutrients. The second nutrient mixture preferably comprises an amount of between approximately 0.001% and approximately 0.01% by weight.

The fermentation medium may further comprise a micronutrient mixture comprising manganese, cobalt, copper, and/or a combination thereof, although the invention is not limited to these micronutrients. The micronutrient mixture preferably comprises an amount of between approximately 0.0001% and approximately 0.01% by weight.

The *Capsicum* sp. cultivar preferably comprises 1 part *Capsicum* sp. cultivar to an amount of between approximately 1 and approximately 120 parts water; more preferably between approximately 2 and approximately 50 parts water; and most preferably between approximately 5 and approximately 10 parts water.

The carbohydrate in the fermentation medium preferably comprises an amount of between approximately 1% and approximately 40% by weight; more preferably an amount of between approximately 5% and approximately 20% by weight; and most preferably an amount of between approximately 10% and approximately 15% by weight.

The yeast culture inoculum in the fermentation medium preferably comprises an amount of between approximately 0.11% and approximately 50% by volume; more preferably between approximately 1% and approximately 20% by volume; and most between approximately 5% and approximately 10% by volume.

The nutrient mixture preferably comprises an amount of between approximately 0.1% and approximately 10% by volume and most preferably comprises an amount of between approximately 1% and approximately 5% by volume. The composition of the nutrient mixture is preferably as described above. Likewise, the preferred species of the *Capsicum* is *Capsicum chinense*.

The present invention is further directed to a method for preparing a topical pain relief composition. This method preferably comprises preparing a capsaicin yeast culture inoculum medium; preparing a capsaicin fermentation medium; inoculating the fermentation medium with the yeast culture inoculum; incubating the yeast culture in the fermentation medium; extracting the volatile fermentation products and by-products from the fermentation medium; and blending the fermentation volatile fermentation products and by-products into an oil to form a topical pain relief composition.

Preparing the yeast culture inoculum medium preferably comprises adding a *Capsicum* sp. to water to form a mixture; adding a nutrient mixture comprising at least one nutrient selected from the group consisting of nitrogen, phosphorus, potassium and a combination there, to the mixture; sterilizing the mixture; cooling the mixture; adding a yeast to the mixture; and incubating the mixture.

The *Capsicum* sp. cultivar is preferably in an amount of 1 part *Capsicum* sp. cultivar to an amount of between approximately 1 and approximately 120 parts water; more preferably 1 part *Capsicum* sp. cultivar to an amount of between approximately 10 and approximately 40 parts water; and most preferably 1 part *Capsicum* sp. cultivar to an amount of between approximately 15 and approximately 30 parts water.

The yeast is added preferably in an amount of between approximately 0.1% and approximately 50% by volume; more preferably in an amount of between approximately 0.1% and approximately 50% by volume; and most preferably in an amount of between approximately 1% and approximately 10% by volume.

The nutrient mixture is preferably added in an amount of between approximately 0.1% and approximately 10% by volume; and most preferably in an amount of between approximately 1% and approximately 2% by volume. The nutrient mixture composition is preferably as discussed above. Likewise, the *Capsicum* sp. Is preferably *Capsicum chinense*.

Sterilizing the mixture may comprise autoclaving the mixture.

Incubating preferably occurs at a temperature of between approximately 13° C. and 45° C.; and most at a temperature of between approximately 18° C. and 40° C. The mixture is incubated preferably for between approximately 24 and 96 hours.

The capsaicin fermentation medium is prepared by: adding a *Capsicum* sp. cultivar to water to form a solution; adding a carbohydrate to the solution; adding a nutrient mixture (such as discussed above); pasteurizing the fermentation medium; and cooling the fermentation medium. A second nutrient mixture and/or a micronutrient mixture (such as discussed above) may be added.

The *Capsicum* sp. cultivar is preferably added in an amount of 1 part of the *Capsicum* sp. cultivar to an amount of between approximately 1 and 120 parts water; more preferably 1 part of the *Capsicum* sp. cultivar to an amount of between approximately 2 and 50 parts water; and most preferably 1 part of the *Capsicum* sp. cultivar to an amount of between approximately 5 and 10 parts water.

The carbohydrate, yeast, and nutrient mixture may be added in the amounts and compositions, such as discussed above.

The yeast inocolum is added in an amount of preferably between approximately 0.1% and approximately 50% yeast inoculum by volume; more preferably in an amount of between approximately 1% and approximately 20% yeast inoculum by volume; and most preferably in an amount of between approximately 5% and approximately 10% yeast inoculum by volume.

The yeast is preferably incubated in the fermentation medium comprises incubating for between approximately 24 hours and 3 weeks.

Additional carbohydrates may be added in incremental doses as fermentation slows until a total of between approximately 3 and 50% have been added.

Extracting the volatile fermentation products and by-products from the fermentation medium preferably comprises disposing a layer of oil over the fermentation medium in a ratio of between approximately 1 to approximately 40 parts oil to one part ground *Capsicum* sp.; heating the oil and fermentation medium; and separating the oil phase from the water phase.

Heating the oil and the fermentation medium comprises heating them to a simmering or low boil stage until the water phase has been reduced by an amount between approximately 20% and 80%.

Blending the volatile fermentation products and by-products into an oil comprises blending the fermentation extract containing the volatile fermentation products and by-products into an oil comprising at least one member selected from the group consisting of vegetable oil, butter, margarine, lard, petrolatum, mineral oil, paraffin, wax, liquid hydrocarbon, semi-solid hydrocarbon, and a combination thereof.

Adding the vegetable oil comprises adding an oil selected from the group consisting of corn oil, canola oil, peanut oil, soy oil, palm oil, sesame oil, and a combination thereof.

The step of blending the extract into the oil comprises blending one part of the fermentation extract into an amount of between approximately 5 parts to 10,000 parts of the oil.

A primary object of the present invention is to provide for topical pain relief using oil soluble constituents of cultivars of the genus *capsicum*.

A primary advantage of the present invention is that a full spectrum of oil soluble fermentation products including whole capsaicin may be topically applied for the treatment of pain.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

The present invention relates to a pain balm using cultivars of the genus *capsicum*. All species of *capsicum*, including those whose cultivars have Scoville units from 5,000 to 600,000 may be used. In the preferred embodiment, *Capsicum chinense* (i.e., habanero) is used. The *Capsicum* sp. (ground) may be either fresh or dried. Although the term "balm" is used throughout this application, it should be understood that any medium form useable for the topical application of the capsaicin fermentation extract of the present invention may be used.

In addition to a cultivar of *Capsicum* sp., the reagents and components of the present invention preferably comprise one or more of the following:

1. *Capsicum* sp. in water in a ratio of from approximately one part *Capsicum* sp. to 1 to 120 parts water. The amount of *Capsicum* sp. may vary depending on the desired strength of the balm and depending on *Capsicum* sp used as different species contain different Scoville Units.

2. a yeast culture inoculum to provide from approximately 0.11% to approximately 50% of the composition's total volume.

3. a fermentable carbohydrate to provide approximately 1% to approximately 40% of the composition's total weight.

4. a balanced source of primary nutrients preferably comprising nitrogen (N), phosphorous (P), and potassium (K) (in, for example, a 20-20-20 mixture), to provide approximately 0.1 to 10% of the composition's total weight.
5. secondary nutrients comprising one or more of calcium at approximately 0.001 to 0.1%, magnesium at approximately 0.001 to 0.1%, iron at approximately 0.001 to 0.1%, and/or zinc at approximately 0.001 to 0.1% of the composition's total weight.
6. a micronutrient mixture comprising one or more of manganese at approximately 0.0001 to 0.01%, cobalt at approximately 0.0001 to 0.01%, and/or copper at approximately 0.0001 to 0.01% of the composition's total weight.
7. an oil, such as vegetable oil (e.g., corn oil, canola oil, peanut oil, soy oil, palm oil, sesame oil), butter, margarine, lard, petrolatum, mineral oil, paraffin, waxes and/or other liquid or semi-solid hydrocarbons in a ratio of approximately five to 10,000 parts oil to one (1) part *Capsicum* sp.

In the preferred embodiment of the present invention, the procedure for preparing the pain balm of the present invention is as follows:

A yeast inoculum is prepared for the inoculation of a fermentation medium containing carbohydrates and capsaicin. A suspension of ground *Capsicum* sp., preferably habanero (300,000 to 600,000 Scoville units), is prepared at a ratio of preferably between approximately 1 part *Capsicum* sp. to between approximately 1 part and approximately 120 parts water, preferably between approximately 10 parts and approximately 40 parts water, and more preferably still between approximately 15 parts and approximately 30 parts water. Primary nutrients are added in preferably a final concentration of between approximately 0.1% and approximately 10% by weight, and more preferably between approximately 1% and approximately 2% by weight. The suspension is sterilized by any method known in the art such as by heating in an autoclave at for example, approximately 134° C. for approximately 15 to 30 minutes. The suspension is cooled to preferably room temperature. The suspension is inoculated with a yeast culture to comprise preferably between approximately 0.1% and approximately 50% of the total suspension volume, more preferably between approximately 1% and approximately 20%, and still more preferably between approximately 5% and approximately 10%. The yeast and medium are incubated at a suitable temperature such as, for example, at between approximately 13° C. and approximately 45° C., preferably between approximately 18° C. and approximately 40° C., and more preferably between approximately 10° C. and approximately 15° C., for preferably between approximately 24 and approximately 96 hours (or until vigorous fermentation has ceased).

To prepare the fermentation medium, a carbohydrate is dissolved in water to provide a solution of between approximately 1% to approximately 40% carbohydrate by weight, preferably between approximately 5% and 20% by weight, and still more preferably between approximately 10% and 15% by weight. Ground *Capsicum* sp., preferably ground habanero (300,000 to 600,000 Scoville units), is added to the sugar solution to provide a final ratio of approximately 1 part *Capsicum* sp. to preferably between approximately 1 part and approximately 120 parts water, more preferably between approximately 2 parts and approximately 50 parts water, and more preferably still between approximately 5 parts and approximately 10 parts water. The ground *Capsicum* sp. is added so that it can be subjected to reactions associated with fermentation by the yeast. A nutrient mixture is preferably added comprising nitrogen, phosphorus, and/or potassium, preferably in an amount of 20-20-20 nitrogen-phosphorus-potassium. The nutrient mixture is added to comprise preferably between approximately 0.1% and approximately 10%, and more preferably between approximately 1% and approximately 5%, nutrient mixture by weight. A secondary nutrient mixture is preferably added comprising one or more of calcium, magnesium, iron, and/or zinc at preferably approximately 0.001 to 0.1% by weight. A micronutrient mixture is also added comprising one or more of manganese, cobalt, and/or copper at preferably approximately 0.0001 to 0.01% by weight.

The solution is pasteurized by heating at, for example, 25 minutes at 95° C. for 25 minutes. The solution is then cooled to, for example, between approximately 20° C. and 40° C. The solution is inoculated with the yeast inoculum so that the yeast inoculum comprises approximately 10% of the solution's total volume. The solution is incubated at preferably approximately 20° to 40° C. for preferably approximately one to three weeks.

The fermentation solution is preferably observed daily. Preferably, gas evolution observably occurs within 24 hours of incubation and should continue until the carbohydrate is depleted. Preferably, as fermentation slows to the point where a reduction of gas bubbles is observed, carbohydrate is incrementally added in concentrations (of, for example approximately 2.5% to 5% by weight) to continue fermentation. The addition of carbohydrate is repeated with each occurrence of reduced or stopped fermentation until a total of between approximately 1% and approximately 50% by weight, preferably between approximately 10% and approximately 20% by weight, and still more preferably between approximately 13% and approximately 16% by weight of carbohydrate has been added. Incubation should preferably be continued until the fermentation comes to a complete stop. Typically, fermentation stops approximately two to three weeks after inoculation. The duration of fermentation depends in large part on the temperature.

Upon completion of the fermentation, capsaicin and other volatile fermentation by products such as capsaicin co-factors and capsaicin analogs are extracted from the fermentation mixture. Preferably, the fermentation mixture is placed in a container suitable for heating, and oil (hydrocarbon) is layered over the fermentation liquor. Solid or semi-solid oils or hydrocarbons are heated to the melting point before layering them over the fermentation liquor. The oil is added to provide a ratio of preferably between approximately 1 part and approximately 40 parts, more preferably between approximately 2 parts and approximately 20 parts, and still more preferably between approximately 8 parts and approximately 12 parts oil to approximately one part ground *Capsicum* sp. (preferably Habanero).

The fermentation mixture preferably over-layered with the hydrocarbon oil is heated to a simmering or low boil stage. Heat is maintained to hold the liquid at the simmering stage for up to approximately one hour or until the water phase has been reduced by between approximately 20% and approximately 80%, preferably between approximately 30% and approximately 70%, and still more preferably between approximately 40% and approximately 60%, at which time the oil phase should be separated from the water phase. The oil phase, referred to herein as the capsaicin fermentation extract, contains the volatile, oil soluble fermentation products and is used to prepare the final product.

The final product is preferably prepared as a cream, salve, ointment, balm, oil spray or topical oil rub and packaged accordingly. The product from the distillation/extraction procedure is blended into a vegetable oil, petrolatum, waxes, paraffin or hydrocarbons at concentrations ranging from preferably between approximately 0.001% and approximately 30%, more preferably between approximately 0.01% and approximately 20%, still more preferably between approximately 0.1% and approximately 10%. The product is topically applied to feet, ankles, calves, knees, thighs, hips, lower back, neck, shoulders, elbows, wrist and hands for the reduction of itching, muscle pain, and/or joint pain.

EXAMPLES

Three formulations of pain balm were prepared for evaluation and experimental purposes to alleviate or prevent pain. One formulation was prepared according to the preferred procedure to provide a final product for distillation that contained a ratio of three parts habanero to 100 parts petrolatum (i.e., 3% habanero pain balm). The second formulation comprised 2 parts habanero to 100 parts petrolatum (i.e., 2% habanero pain balm). The third formulation comprised one part habanero to 100 parts petrolatum (i.e., 1% habanero). The three formulations were used as test samples for evaluate the formulations on various types of pain.

Example 1

A male individual who had received open heart surgery and was experiencing post surgical pain on the surgical scar had tried a variety of topical creams that allegedly suppressed pain, including capsaicin creams. Having received no pain relief, he turned to a pain specialist who provided several systemic painkillers. He received no satisfactory relief. The level of pain was such that he was unable to wear a shirt or other clothing over the wound thus preventing him from returning to his job. He was provided with the 1% pain balm, and he applied it topically four times daily. Having received pain relief that enabled him to wear a shirt and other clothing without irritation, he requested a larger, more concentrated pain balm one week later. He was then provided with a 2% pain balm. The 2% pain balm was so effective that he was free of the scar neuroma pain and was able to wear clothes including tightly fitting shirts.

Example 2

A pain specialist physician experimented with other patients using the balm of the present invention. He found that the 3% habanero pain balm was a good concentration for general use in treating patients experiencing pain.

Example 3

A female in her late 50s who was experiencing carpal tunnel syndrome symptom-like pain in both wrists applied a 3% pain balm to one wrist. Within one hour, she noted the complete disappearance of pain in that wrist and applied the pain balm to the second wrist. She continued using a light application of the pain balm to her wrist in the morning before going to work with the effect of being pain-free for the duration of her workday. In instances where she experience pain at bedtime, she applied more pain balm before going to sleep, and she slept comfortably.

Example 4

A female in her early 60s experiencing upper back and neck pain was unable to take any pain medication because of the sensitivity of her stomach to all pain medication. She applied the 3% habanero pain balm to the painful region, and within one hour experienced no more neck and upper back pain. She continued applying the pain balm to her neck and back daily before going to work, and she remained pain-free during the workday.

Example 5

A 52-year-old high school teacher and coach had suffered with a three-year history of left hip pain and was diagnosed by two different orthopedic specialists as having a vascular necrosis of the left hip. Notwithstanding his pain, he insisted on continuing to jog 120 miles weekly. He applied the habanero pain balm to his hip before running and received relief that lasted during his long runs and for the remainder of the day.

Example 6

A 65-year old male suffered a torn rotator cuff to the right shoulder. Pain from the rotator tear severely inhibited range of motion and the ability to lift anything in excess of two pounds. The pain also awakened him from sleep when he changed positions during the night. He applied the habanero pain balm to his shoulder before bedtime and experienced such a reduction in pain that he was able to sleep uninterrupted by pain. His daytime activities were enhanced through the application of the habanero balm to the shoulder each morning. He was able to lift significantly heavier objects without experiencing pain.

Example 7

This individual described in Example 6 had surgery to repair the rotator cuff. He applied the habanero balm to the shoulder area after surgery and reduced post surgical pain to such an extent that he had no need for oral painkillers (Tylenol plus codeine or Percocet).

Example 8

A 52-year-old disabled former construction worker with chronic and severe knee pain had 4 surgeries on the left knee and 5 on the right knee. He had painful numbness about both knees which he described as burning, stinging, numb, steady and distracting. At one point he was unable to walk for approximately 20 months. He had unsuccessfully used narcotic medications and anti-inflammatory medications. After applying the habanero pain balm, his pain abated significantly. Over time, he experienced an increase in the duration of relief and continued to apply the pain balm approximately every six hours.

Example 9

A woman with refractory shoulder pain described the pain as intense with spasms in the neck/shoulder area. Twelve years prior to using the pain balm, she had undergone cervical and thoracic spine surgery which did not resolve her pain. Prior pain treatment had included extensive pain management interventions at a pain clinic, but the treatment was unsuccessful. Because she had a history of the venous thrombosis which required her to take coumadin, 6 mg three times weekly and 5½ mg four times weekly, and suffered from significant osteoporosis, procedures such as epidural steroid injections or injection therapy were contraindicated. After she applied the habanero pain balm to her neck and shoulders, she received relief from the pulling, painful spasms as well as the pins and needles sensation at the base of her neck. She expressed joy at her relief of pain.

Example 10

An elderly man, who suffered frostbite in the Battle of the Bulge in World War II, had significant painful neuropathic symptoms affecting the feet and hands. He also suffered a mild stroke and had high blood pressure and atrial fibrillation. He applied the habanero pain balm to his feet. The pain balm provided relief throughout the night. He reported no side effects from the pain balm.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A composition for a topical pain treatment comprising:
   an oil; and
   a fermentation mixture, said fermentation mixture comprising:
      a yeast culture;
      a *Capsicum* sp. cultivar in water; and
      a nutrient mixture; and
   wherein said oil forms a discrete layer on said fermentation mixture so that said oil receives and holds capsaisin and volatile fermentation byproducts extracted from said fermentation mixture; and
   wherein said oil, being layered on said fermentation mixture and substantially unmixed with said fermentation mixture, is separable from said fermentation mixture for application as a topical pain treatment.

2. The composition of claim 1 wherein said fermentation mixture further comprises a carbohydrate.

3. The composition of claim 1 further comprising a second nutrient mixture comprising at least one member selected from the group consisting of calcium, magnesium, iron, zinc and a combination thereof.

4. The composition of claim 3 wherein said second nutrient mixture comprises an amount of between approximately 0.001% and approximately 0.01% by weight.

5. The composition of claim 1 further comprising a micronutrient mixture.

6. The composition of claim 5 wherein said micronutrient mixture comprises an amount of between approximately 0.0001% and approximately 0.01% by weight.

7. The composition of claim 1 wherein said *Capsicum* sp. cultivar comprises 1 part *Capsicum* sp. cultivar to an amount of between approximately 1 and approximately 120 parts water.

8. The composition of claim 7 wherein said *Capsicum* sp. cultivar comprises 1 part *Capsicum* sp. cultivar to an amount of between approximately 2 and approximately 50 parts water.

9. The composition of claim 8 wherein said *Capsicum* sp. cultivar comprises 1 part *Capsicum* sp. cultivar to an amount of between approximately 5 and approximately 10 parts water.

10. The composition of claim 2 wherein said carbohydrate comprises an amount of between approximately 1% and approximately 40% by weight.

11. The composition of claim 10 wherein said carbohydrate comprises an amount of between approximately 5% and approximately 20% by weight.

12. The composition of claim 11 wherein said carbohydrate comprises an amount of between approximately 10% and approximately 15% by weight.

13. The composition of claim 1 wherein said yeast culture comprises an amount of between approximately 0.11% and approximately 50% by volume.

14. The composition of claim 13 wherein said yeast culture comprises an amount of between approximately 1% and approximately 20% by volume.

15. The composition of claim 14 wherein said yeast culture comprises an amount of between approximately 5% and approximately 10% by volume.

16. The composition of claim 1 wherein said nutrient mixture comprises an amount of between approximately 0.1% and approximately 10% by volume.

17. The composition of claim 16 wherein said nutrient mixture comprises an amount of between approximately 1% and approximately 5% by volume.

18. The composition of claim 1 wherein said *Capsicum* sp. comprises *Capsicum chinense*.

19. The composition of claim 1 wherein a ratio of said *Capsicum* sp. cultivar to said oil is of one part *Capsicum* sp. cultivar to from between approximately 5 parts and approximately 10,000 parts of said oil.

20. The composition of claim 1 wherein said nutrient mixture comprises nitrogen.

* * * * *